US010702208B2

(12) United States Patent
Kortelainen et al.

(10) Patent No.: US 10,702,208 B2
(45) Date of Patent: Jul. 7, 2020

(54) APPARATUS AND METHOD FOR ELECTROENCEPHALOGRAPHIC EXAMINATION

(71) Applicant: CERENION OY, Oulu (FI)

(72) Inventors: Jukka Kortelainen, Oulu (FI); Eero Väyrynen, Oulu (FI); Tapio Seppänen, Oulu (FI)

(73) Assignee: CERENION OY, Oulu (FI)

( * ) Notice: Subject to any disclaimer, the term of this patent is extended or adjusted under 35 U.S.C. 154(b) by 281 days.

(21) Appl. No.: 14/674,318

(22) Filed: Mar. 31, 2015

(65) Prior Publication Data

US 2016/0287169 A1    Oct. 6, 2016

(51) Int. Cl.
| | | |
|---|---|---|
| *A61B 5/00* | (2006.01) |
| *A61M 16/01* | (2006.01) |
| *A61B 5/04* | (2006.01) |
| *A61B 5/0476* | (2006.01) |
| *A61M 16/10* | (2006.01) |
| *A61B 5/048* | (2006.01) |

(Continued)

(52) U.S. Cl.
CPC ........ *A61B 5/4821* (2013.01); *A61B 5/04012* (2013.01); *A61B 5/0476* (2013.01); *A61B 5/4064* (2013.01); *A61B 5/4839* (2013.01); *A61B 5/7275* (2013.01); *A61M 16/01* (2013.01); *A61M 16/104* (2013.01); *A61B 5/0042* (2013.01); *A61B 5/048* (2013.01); *A61M 5/1723* (2013.01); *A61M 2230/005* (2013.01); *A61M 2230/10* (2013.01); *G16H 50/30* (2018.01)

(58) Field of Classification Search
None
See application file for complete search history.

(56) References Cited

U.S. PATENT DOCUMENTS

| | | | | |
|---|---|---|---|---|
| 4,869,264 A | * | 9/1989 | Silberstein | A61B 5/04842 600/544 |
| 6,016,444 A | * | 1/2000 | John | A61M 16/104 128/910 |

(Continued)

FOREIGN PATENT DOCUMENTS

| | | |
|---|---|---|
| EP | 2789293 A1 | 10/2014 |
| WO | 01/058351 A1 | 8/2001 |

(Continued)

OTHER PUBLICATIONS

Kaier Wang, EEG slow-wave coherence changes in propofol-induced general anesthesia: experiment and theory, Oct. 29, 2014, Frontiers in Systems Neuroscience, vol. 8, pp. 1-16.*

(Continued)

*Primary Examiner* — Christian Jang
*Assistant Examiner* — Sarah R Kingsley
(74) *Attorney, Agent, or Firm* — Oliff PLC

(57) ABSTRACT

An apparatus comprises a data processing unit (100) which receives electroencephalographic data based on a measurement of a person (110) exposed to anesthetic drug substance which has one or more estimated or measured non-zero levels of concentration in the body (108) of the person (110) as a function of time; and determines and present activity of slow waves of the electroencephalographic data at the one or more estimated or measured levels of the non-zero concentration of the anesthetic drug substance.

13 Claims, 4 Drawing Sheets

(51) Int. Cl.
*G16H 50/30* (2018.01)
*A61M 5/172* (2006.01)

(56) References Cited

U.S. PATENT DOCUMENTS

| | | | | |
|---|---|---|---|---|
| 6,071,933 | A * | 6/2000 | Joo | A61K 31/445 514/329 |
| 6,248,345 | B1 * | 6/2001 | Goldenheim | A61K 9/0019 424/426 |
| RE41,291 | E * | 4/2010 | Viertio-Oja | A61B 5/0476 600/544 |
| 2002/0017296 | A1 * | 2/2002 | Hickle | A61B 5/417 128/203.12 |
| 2002/0117176 | A1 | 8/2002 | Mantzaridis et al. | |
| 2002/0173729 | A1 | 11/2002 | Viertio-Oja et al. | |
| 2003/0181821 | A1 * | 9/2003 | Greenwald | A61B 5/048 600/544 |
| 2006/0009709 | A1 * | 1/2006 | Rautee | A61B 5/0476 600/544 |
| 2006/0217628 | A1 | 9/2006 | Huiku | |
| 2007/0167853 | A1 * | 7/2007 | Melker | A61B 5/082 600/532 |
| 2007/0208322 | A1 * | 9/2007 | Rantala | A61M 5/1723 600/544 |
| 2013/0331660 | A1 | 12/2013 | Al-Ali et al. | |
| 2014/0187973 | A1 * | 7/2014 | Brown | A61B 5/0476 600/483 |
| 2014/0316217 | A1 * | 10/2014 | Purdon | A61B 5/4821 600/301 |
| 2015/0140127 | A1 * | 5/2015 | Ramirez | G01N 33/6896 424/663 |

FOREIGN PATENT DOCUMENTS

| | | |
|---|---|---|
| WO | 20061094797 A1 | 9/2006 |
| WO | 2013/179048 A1 | 12/2013 |

OTHER PUBLICATIONS

E. Mortier, Closed-loop controlled administration of propofol using bispectral analysis, 1998, Blackwell Science, 53, pp. 749-754.*

Jukka Kortelanien, Pilot Study of Propofol-induced Slow Waves as a Pharmacologic Test for Brain Dysfunction after Brain Injury, Jan. 2017, Anesthesiology, vol. 126, pp. 94-103. (Year: 2017).*

Jun. 21, 2016 International Search Report issued in International Application No. PCT/FI2016/050194.

Holschneider, D.P., et al. "Attenuation of brain high frequency electrocortical response after thiopental in early stages of Alzheimer's dementia". Psychopharmacology. vol. 149, No. 1, s. 6-11. Mar. 2000.

Snaedal, J., et al. "The use of EEG in Alzheimer's disease, with and without scopolamine—A pilot study". Clinical Neurophysiology 121, pp. 836-841. 2010.

Oct. 12, 2018 Supplementary European Search issued in European Application No. 16771456.

J. Gareth Jones, M.D., "Awareness Under Anaesthesia," Anaesthesia Rounds. No. 21, Nov. 21, 1989.

Feb. 19, 2019 Office Action issued in Japanese Patent Application No. 2017-551699.

* cited by examiner

APPARATUS AND METHOD FOR ELECTROENCEPHALOGRAPHIC EXAMINATION

FIELD

The invention relates to an apparatus and a method for electroencephalographic examination.

BACKGROUND

Assessing function of the brain of a person with a potential injury caused by a cardiac arrest, a stroke, trauma or the like remains a significant medical challenge. Appropriate treatment, therapeutic interventions and even their development as well as recovery of the person depend on a reliable and early detection of a brain dysfunction.

Modern brain imaging techniques enable the assessment the brain function. However, the imaging techniques are laborious and expensive, and an imaging device is fixed to its position and is thus non-movable. A person with brain injury, in turn, is typically a patient of an intensive care unit whose health doesn't allow his/her movement. The combination makes it challenging or impossible to take the person to the brain examination and set him/her in a proper position in the imaging device. Furthermore, the brain imaging at least almost always requires movement of the person to a different room typically outside the intensive care unit. Thus, a need exists to develop the examination of the brain function of a person with a potential brain injury.

BRIEF DESCRIPTION

The present invention seeks to provide an improved monitoring system and monitoring method. According to an aspect of the present invention, there is provided an apparatus as specified in claim 1.

The invention also relates to a brain examination apparatus according to claim 12.

The invention further relates to a method according to claim 13.

Preferred embodiments of the invention are disclosed in the dependent claims.

The solutions according to the invention provide several advantages. It is possible to determine and present the slow wave activity of the brain with respect to one or more concentrations of the anesthetic drug substance which may be used for further actions.

LIST OF DRAWINGS

Example embodiments of the present invention are described below, by way of example only, with reference to the accompanying drawings, in which FIG. 1 illustrates an example of a measurement with the apparatus;

DESCRIPTION OF EMBODIMENTS

The following embodiments are only examples. Although the specification may refer to "an" embodiment in several locations, this does not necessarily mean that each such reference is to the same embodiment(s), or that the feature only applies to a single embodiment. Single features of different embodiments may also be combined to provide other embodiments. Furthermore, words "comprise" and "include" in their different forms should be understood as not limiting the described embodiments to consist of only those features that have been mentioned and such embodiments may contain also features/structures that have not been specifically mentioned.

The following embodiments are presented by way of example. Even though the description may refer to "a", "one", or "same" embodiment or embodiments at different points, this does not necessarily mean that each such reference is made to the same embodiment or embodiments or that a feature only applies to one embodiment. Individual features of different embodiments may also be combined to enable other embodiments.

Slow waves, the frequency f of which is at or below 1 Hz (f<1 Hz), may be considered one of the most important EEG signatures of non-rapid eye movement (NREM) sleep. Based on the physiological importance of the slow waves and the possibility to test their generation with anesthetics in a controlled manner, it can be hypothesized that this electrophysiological phenomenon is disrupted in an injured brain. The synchronized activity of large neuronal populations as well as the delicate interaction between cortical and sub-cortical areas required in the formation of the waves can be expected to be sensitive to abnormal brain function. For this purpose, this application refers to an experiment carried out with a plurality of comatose patients of an intensive care unit (ICU) after resuscitation from out-of-hospital cardiac arrest.

The experimental protocol was approved by the institutional Ethics Committee of Oulu University Hospital which follows the Declaration of Helsinki guidelines. The patients' closest relatives were asked for an informed written consent to participate. Because of the reduced oxygen supply during the cardiac arrest, the patients potentially had suffered from hypoxic-ischemic brain injury due to which they had received therapeutic hypothermia treatment as a neuroprotective measure before the experiment. These patients generally represent a substantial diagnostic challenge as detecting the potential diffuse brain injury in the early phase of recovery is highly demanding. In the experiment, the patients' ability to generate anesthetic-induced slow waves was tested by exposing them to varying amounts of anesthetic drug substance (propofol) in a controlled manner. To assess the association between the slow waves and brain injury, the patients' neurological recovery was then followed for six months.

Figure 1:
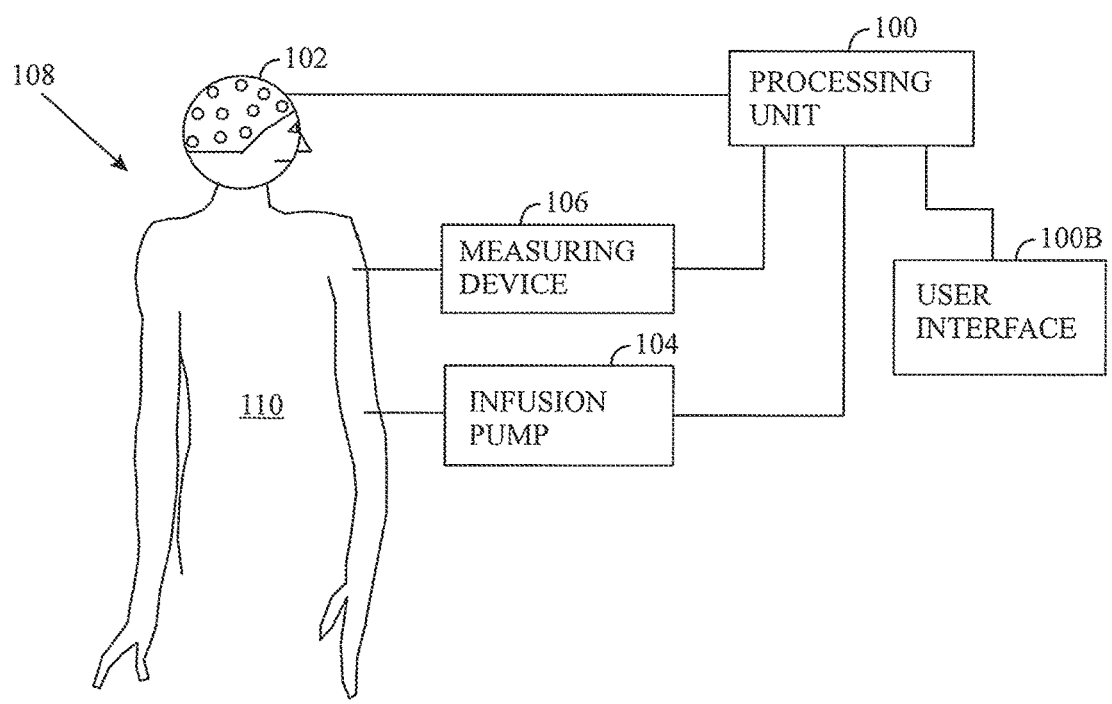

Examine now an apparatus for brain examination by means of FIG. 1. The apparatus comprises a data processing unit 100, and in an embodiment the apparatus may also comprise electrode system 102, an administration device 104 and/or a blood measuring device 106. The administration device 104 may include or be an infusion pump, for example.

The electrode system 102 is electrically coupled or in contact with the scalp or the brain of a person 108. The electrode system 102 provides the electroencephalographic (EEG) data for the data processing unit 100. The electroencephalographic data may be directly fed from the electrode system 102 to the data processing unit 100 or the electroencephalographic data may first be stored in memory and the electroencephalographic data may later be fed to the data processing unit 100.

Electroencephalography, per se, is a recording of electrical activity of the brain. The electrical activity is measured as a voltage variation caused by the neurons of the brain tissue.

Electroencephalographic data refers to electroencephalographic information which is in an analog or a digital form which can be processed and analyzed in the data processing unit 100. The measured data is processed and analyzed in the data processing unit 100 for determining state(s) of the brain and/or its function. A control action, a decision, result data or a diagnosis may be based on the electroencephalographic data or the determined state(s)/function.

To record EEG signal the system may have a plurality of channels like in the experiment. The number of channels may be 19, without restricting to that. The EEG may be recorded according to the 10/20 international system using an electrode cap with Ag/AgCl electrodes as the electrode system 102. For the recording, Nicolet nEEG Modular Neurodiagnostic System with a v32 Amplifier may be used. The amplifier may have a sampling frequency of 500 Hz and bandwidth of 0.053-500 Hz. A common average reference may be used. For the EEG recording, the patient's sedation is realized with an anesthetic drug substance which may follow the ICU's common practice.

The infusion pump may infuse the anesthetic drug substance, which is in a fluidal form, into the body of the person. The anesthetic drug substance comprises one anesthetic drug or a combination of anesthetic drugs. The anesthetic drug substance may be infused into at least one vein of a circulatory system of the person. The anesthetic drug substance may be infused continuously or may be introduced as one or more boluses. The anesthetic drug substance may then be called an intravenous drug substance. Additionally or alternatively arterial, epidural and/or subcutaneous, intrathecal and muscular infusion may be used. Infusion in this context also includes injection. The infusion pumps can administer anesthetic drug substances very accurately. Manual injections of the anesthetic drug substance are more inaccurate and expensive. Infusion pumps can be used to administer the anesthetic drug substance adaptively such that the input varies with respect to a desired parameter such as time, EEG measurement and the measured concentration of the anesthetic drug substance, for example.

Additionally or alternatively, an inhalation device as the administration device 104 may be used for inhaling the anesthetic drug substance. The inhalation may be continuous or the anesthetic drug substance may be introduced in a step-wise manner; each step increasing or decreasing the dose.

The data processing unit 100 receives electroencephalographic data based on an EEG measurement of a person 108. The person 108 is exposed to at least one anesthetic drug substance. The at least one anesthetic drug substance may have one or more estimated or measured non-zero levels of concentration in the body 108 of the person 110 as a function of time. It is possible to measure the EEG in only one non-zero concentration. Instead of one level of concentration, the anesthetic drug substance may have a plurality of concentration levels as a function of time. The at least one concentration level may be estimated or measured. The EEG effect of the anesthetic drug substance depends on its concentration level in the body 108. The EEG characteristics such as burst suppression pattern may be used for determining the effect or level of the anesthetic drug. The EEG characteristics such as a burst suppression pattern may be used for administration of the anesthetic drug substance.

In an embodiment, the at least one anesthetic drug substance may be administered so much that the burst suppression pattern is observed in the EEG measurement. The data processing unit 100 or a nursing staff may make the observation of the burst suppression pattern.

The data processing unit 100 forms and presents a result of a measurement of activity of slow waves of the electroencephalographic data for at the one or more estimated or measured amounts associated with the at least one anesthetic drug substance. The formed and presented result may be in a form of result data. Each amount associated with the at least one anesthetic drug substance may be estimated on the basis of a level of non-zero concentration or on one or more inputs of the at least one anesthetic drug substance introduced to the person 110. The data processing unit 100 may present the result data using at least one variable or index. The zero-concentration of the anesthetic drug substance in the body 108 of the person 110 may be used as a reference. In an embodiment, the data processing unit 100 may form the result data at an amount which causes the burst suppression pattern.

The data processing unit 100 may comprise a user interface 100B which may be used to present the result data visibly, audibly and/or in a written form. The user interface 100B may include a screen, a loudspeaker and/or a printer for presenting the information.

The data processing unit 100 may comprise a computer comprising at least one processor and memory. Their operation is based on a sequence of program commands of the computer program controlling the operation, stored in the memory.

Instead of or in addition to using a processor and memory, controlling may be implemented as one or more integrated circuits, such as an application-specific integrated circuit ASIC. Other equipment embodiments are also feasible, such as a circuit constructed of separate logic devices. A hybrid of these different implementations is also possible.

In an embodiment, the administration device 104 may adjust an input of the anesthetic drug substance which is introduced into the body 108. The term "input" refers to an infusion rate or dosing of the anesthetic drug substance. In this manner, the concentration or the EEG effect of the anesthetic drug substance in the body 110 at a certain moment may be estimated and controlled on the basis of the adjusted input.

In an embodiment, the adjusting of the input includes adjusting an amount of the anesthetic drug substance per time unit. In an embodiment, the adjusting of the input includes adjusting an amount of the anesthetic drug substance on the basis of EEG characteristics such as burst suppression pattern. The input may depend on a type of the anesthetic drug or combination of anesthetic drugs. In an embodiment, the adjusting of the doses includes the adjusting an administration frequency of the doses of the anesthetic drug substance. The rate of the doses may be varying as a function of time, for example. The introduction of the anesthetic drug substance causes the one or more levels of concentration of the anesthetic drug substance in the body of the person.

The EEG effect of the at least one anesthetic drug substance may be estimated on the basis of the input. The EEG effect depends on the concentration of the anesthetic drug substance in the brain or in blood which, in turn, depends on the input.

Figure 2:
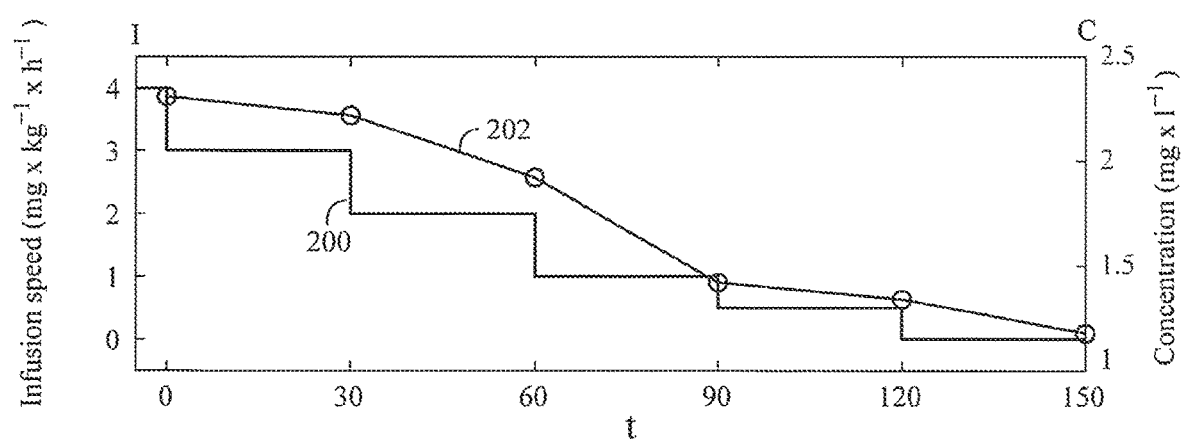
FIG. 2 illustrates an example of input of the infusion pump and the concentration of the anesthetic drug substance in blood.

FIG. 2 illustrates examples a curve 200 of input of the anesthetic drug substance with an infusion pump and a curve 202 of concentration of the anesthetic drug substance in blood of a person with good outcome. The first vertical axis denotes input I defined by the mass unit (mg) of the anesthetic drug substance per both time unit (h) and the mass unit (kg) of the person to whom the anesthetic drug substance is administered. The second vertical axis denotes the concentration C (mg/l) of the anesthetic drug substance in blood. The horizontal axis denotes time T in minutes. In this experiment only one anesthetic drug was used, and the anesthetic drug was propofol. The amount of administered propofol was decreased step-wise from 4 mg/kgh to 0 mg/kgh in every 30 min. The dosing of the anesthetic drug substance may decrease in every step the same amount. The dosing of propofol may decrease in every step the same amount, for example about 1 mg/kgh. The dosing of propofol decreased first 1 mg/kgh and then 0.5 mg/kgh in the example of FIG. 2. The concentration of propofol in blood was measured just before the next decrease of the infusion rate and in the end of the experiment. The highest concentration of propofol 2.39±0.45 mg/l (mean±std) was achieved with the highest the infusion rate 4 mg/kgh and the lowest concentration of propofol 0.98±0.26 mg/l was achieved with the lowest infusion rate 0 mg/kgh. The concentration values between groups, i.e. the patients with good and poor neurological outcome, were comparable. The number of persons 108 in this scientific research was ten.

In an embodiment, the amount of the anesthetic drug substance may instead of decreasing be increased from 0 mg/kgh to a desired maximum level. The dosing may be continuous or discrete i.e. stepwise. In an embodiment, the starting level of the anesthetic drug substance may be at 0 mg/kgh or at some other level, and the amount of the anesthetic drug substance may be increasingly administered until a level of the burst suppression pattern is reached. The burst suppression pattern is detectable in the EEG signal.

Figure 3:
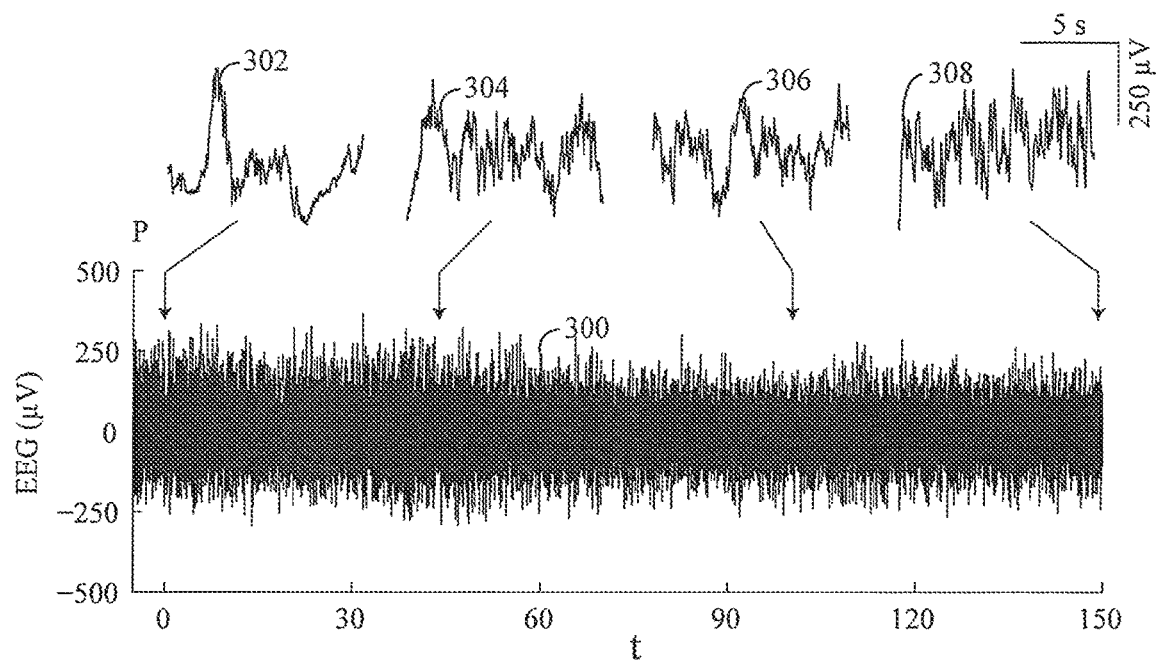
FIG. 3 illustrates an example of EEG signals with respect to decreasing concentration of the anesthetic drug substance in blood.

FIG. 3 illustrates an experimental example of an EEG signal 300 measured from a person with good outcome. The vertical axis denotes strength P of the signal. The strength is measured in microvolts. The horizontal axis denotes time T in minutes and it corresponds to the time axis of FIG. 2. In this way, the EEG may be measured as a function of the concentration of the anesthetic drug substance in blood. The raw EEG may be measured from one or more channels. In an embodiment, a desired number of samples of desired length may be taken from the EEG signal. In this example, four 10-sec signal samples 302, 304, 306, 308 from different phases of the experiment may be selected. They are shown above the continuous signal 300.

In more details, signal samples lasting a few minutes, such as 5 min, may be extracted at each step of the drug infusion rate decrease. The samples may be taken in the end of the 30-min period just before a change in the infusion rate as well as in the end of the experiment corresponding to the collection of the drug concentration blood samples. The period is chosen such that the anesthetic drug substance causes an EEG effect in the person. The period may last from a few minutes to tens of minutes. The EEG samples may be evaluated for abnormalities such as epileptic activity or suppression as well as artifacts automatically or by a clinical neurophysiology specialist. Other artifacts coming from such as EOG (ElectroOculoGraphy) or EMG (ElectroMyoGraphy) may also be removed. From each signal sample, a plurality of representative artifact-free sequences may be picked for further analysis. The sequences may have lengths from seconds to tens of seconds. The length may be 30 sec, for example. These signals may be filtered using a low-pass FIR filter (Finite Impulse Response filter) with a cutoff frequency of 48 Hz, for example, before the calculation of a power spectral density (PSD) estimate using Welch's averaged periodogram method, for example. The estimates may be created using a 5 sec Hamming window or the like and 4.9 sec overlap, for example. An average over said plurality of PSD estimates representing the same infusion rate may then be calculated to improve the robustness of the estimate. From the averaged PSD estimate, the components below or at 1 Hz may be summed to represent low-frequency EEG power. Finally, an average low-frequency power quantifying the patient's slow wave activity at certain infusion rate may be calculated over the all EEG channels. Additionally or alternatively, also other kind of approaches to form one or more variables describing the slow wave activity (<1 Hz) could be used. The slow wave activity may be determined from continuous EEG or bursts occurring during burst suppression pattern. To assess the relative changes in the activity at different infusion rates, the values may be normalized using the individual average powers at the infusion rate 0 mg/kgh of anesthetic drug, substance such as propofol.

The computational EEG analysis may be carried out with Matlab technical computing language and the topographic plots may be made with EEGLAB, for example.

In an embodiment, the data processing unit 100 may measure the activity of the slow waves on the basis of at least one of the following: amplitude spectrum, frequency spectrum, phase spectrum, and a power spectral density of the slow waves. The measurements may include other approaches such as the use of wavelets, empirical mode decomposition and/or low-pass or band-pass filtering for capturing the slow wave activity.

Figure 4:
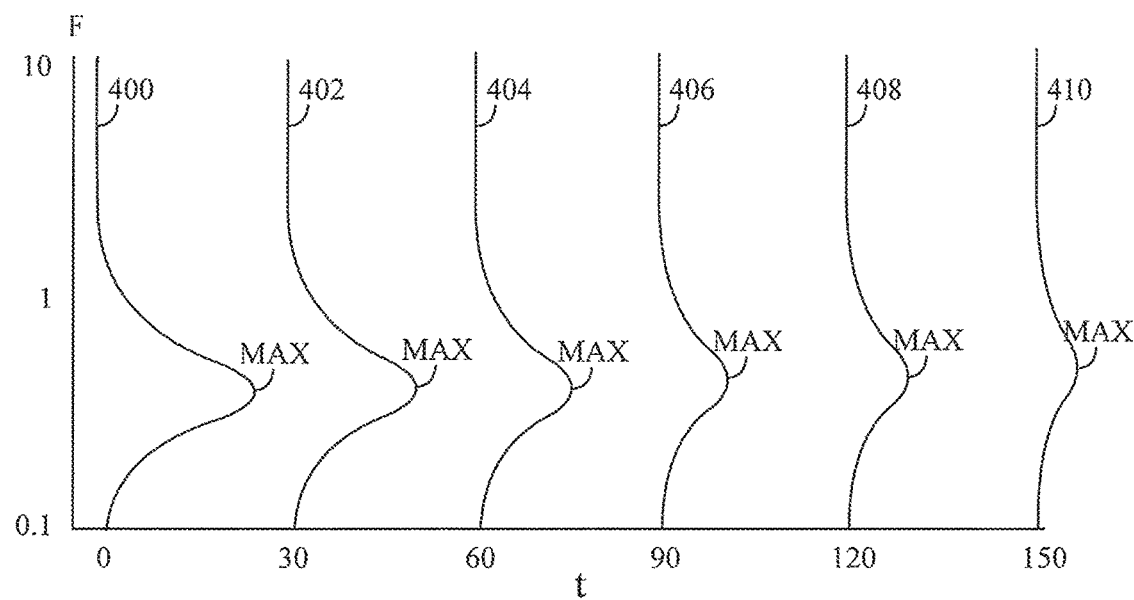
FIG. 4 illustrates an example of slow wave activity with respect to decreasing concentration of the anesthetic drug substance in blood.

FIG. 4 illustrates an example of power spectral density of the activity of the slow waves in the four 10-s signal samples 302-308 of a single channel. The vertical axis denotes frequency F (Hz) in a logarithmic scale. The horizontal axis denotes time t (minutes) in the same and corresponding scale as in FIGS. 2 and 3. The power distribution is shown with the curves 400, 402, 404, 406, 408 and 410. The highest activity is measured in frequencies below 1 Hz although the maximum activity (MAX) and thus its strength or power clearly decreases with decreasing concentration of the anesthetic drug substance in blood. Note that the concentration of the anesthetic drug substance is at its maximums at 0 min and the concentration of the anesthetic drug substance s at its minimum at 150 min as shown in FIG. 2.

Figure 5:
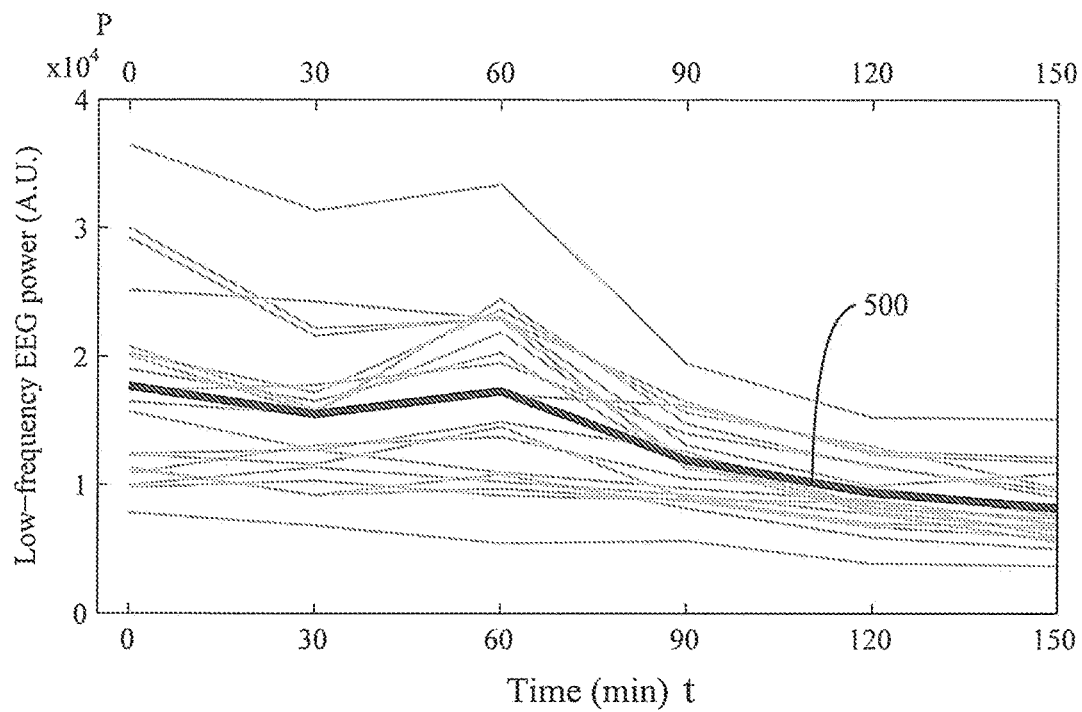
FIG. 5 illustrates an example of decays of the activity of the slow waves in a plurality of channels and the average with decreasing concentration of the anesthetic drug substance in blood.

FIG. 5 illustrates an example of behavior of the power of the activity of the slow waves of a plurality of EEG measurement channels (thin lines) and the average power 500 of the slow waves of the plurality of measurement channels. The vertical axis denotes strength P which can be understood as power in an arbitrary scale. The horizontal axis denotes time T in the same and corresponding scale as in FIGS. 2 to 4. It can be seen that the average power 500 of the slow waves goes down with the decreasing infusing rate and decreasing concentration of the anesthetic drug substance in the blood of the person with good outcome.

In an embodiment, the data processing unit 100 may control the input of the administration device 104. The controlling may set the one or more estimated or measured amounts to input. The controlling may set the one or more estimated or measured levels of the concentration. In this manner, the concentration of the anesthetic drug substance can be controlled precisely with respect to the EEG data, for example.

In an embodiment, the data processing unit 100 may control the administration device 104, for adjusting the input, on the basis of at least one of the following: the EEG, the activity of the slow waves, amount of the anesthetic drug given to the person 110, and data on the concentration of the drug substance in the body 110 of the person 108. The amount of the anesthetic drug given to the person 108 refers to one or more previous infusions or inhalations, and/or boluses.

In an embodiment, the data processing unit 100 may determine a proposed amount of the anesthetic drug which will be given to the person 110, and the data processing unit 100 may control the user interface 100B to present the proposed amount of the anesthetic drug. Then a doctor or some other person of the nursing staff may administer the proposed amount of the anesthetic drug to the person 108.

The input may be based on the concentration of the anesthetic drug substance in the blood of the person 108.

In an embodiment, the blood measuring device 106 receives a blood sample of the person 108, measures the concentration of the anesthetic drug substance in the blood, and feeds the measured data on the concentration of the anesthetic drug substance to the data processing unit 100 which may control the input of the anesthetic drug substance. Or the data processing unit 100 is provided with the information how much anesthetic drug substance is given to the person 110 and the expected EEG response is determined based on that information associated with the anesthetic drug substance.

In an embodiment, the data processing unit 100 may form and output result data. The result data may be used to predict a neurological recovery level of the person 108 on the basis of the activity of the slow waves. The data processing unit 100 presents the result data using the user interface 100B. The neurological recovery level may refer to cerebral performance of the person 108 which may be tested separately.

Below there are some experimental results of patients some of whom had a good neurological outcome after a six-month control period, and some other of whom had a poor neurological outcome after the six-month control period. Those with the best outcome lead independent life with usual activities of daily living without any subjective neurological or psychological deficit due to the event. Those with a poor outcome, on the other hand, have severe anoxic brain injury that lead to permanent coma and finally death during the control period.

Figure 6A:
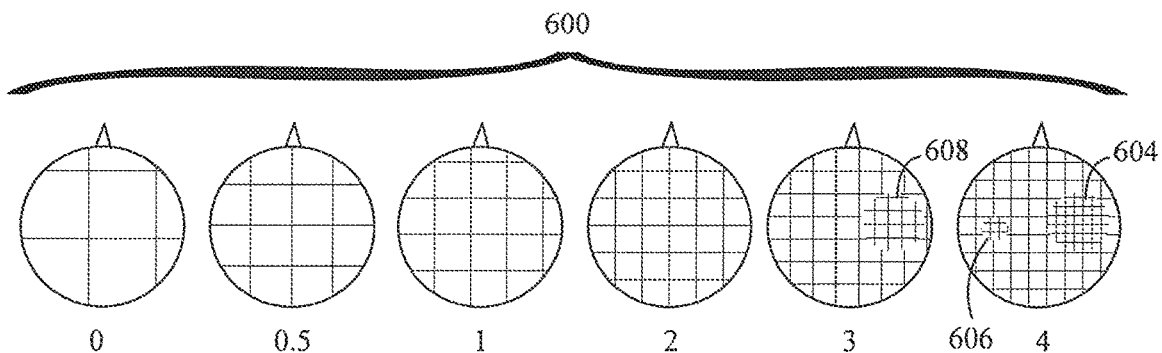
FIG. 6A illustrates an example of a topographic map of the slow wave activity in a brain of good outcome as a function of concentration of the anesthetic drug substance.
Figure 6B:
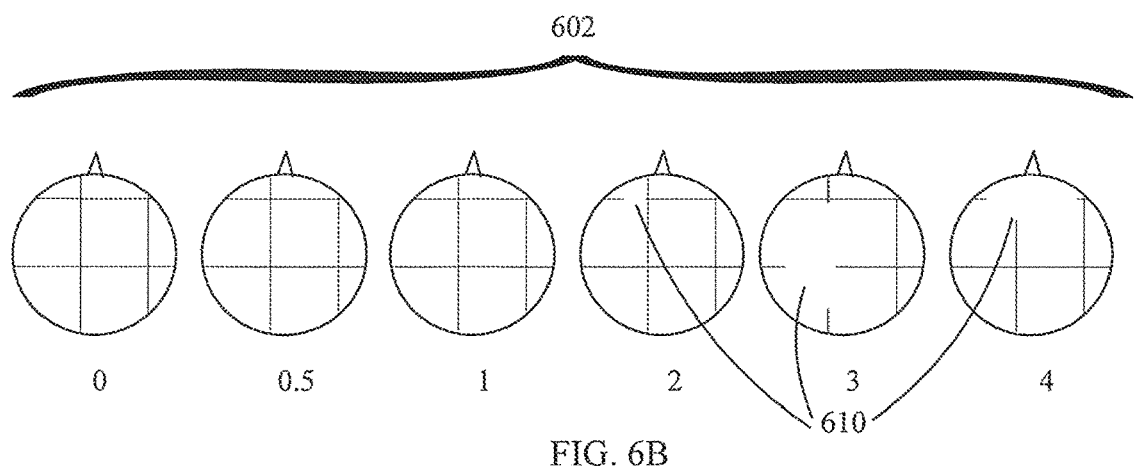
FIG. 6B illustrates an example of a topographic map of the slow wave activity in a brain of poor outcome as a function of concentration of the anesthetic drug substance.

FIGS. 6A and 6B illustrate examples of activity of slow waves in brains of a person with good neurological recovery and a person with a serious and permanent injury. The numbers below the heads denote the infusion rates of an anesthetic drug substance, and the density of the hatching refers to the activity of the slow waves. The activity may differ at different locations of the brain. In FIG. 6A the average measurements 600 of activity of the slow waves which increase as a function of an increasing infusion rate. In locations 604, 606 and 608 the activity has increased up to 400%. FIG. 6B illustrates topographic examples of average measurements 602 of activity of the slow waves which are at least almost constant, don't substantially increase or even decrease as a function of an increasing infusion rate. In the locations 610 the activity has lowered. The infusion rates in the horizontal axis are 0 to 4 mg/kgh. The activity of the slow waves varies 0 to 400 percent with respect to the activity at infusion rate 0 mg/kgh. The neurological recovery of the person of the measurement 600 can be expected to be good. The neurological recovery of the person of the measurement 602 can be expected to be poor.

In an embodiment, the apparatus maps electrical activity across the surface of the brain and forms an EEG topography map.

In an embodiment, the data processing unit 100 may determine location dependent activity of the slow waves across the surface of the brain and form a topographical map of the activity of the slow waves. The topographical map of a person with good recovery may form a characterizing pattern ("fingerprint") which has a disruption in an injured brain. In an embodiment, the data processing unit 100 may determine topographic distribution of the slow waves. Information about the topographic distribution may be included in the result data. For example, phase coupling of different topographic areas may be included in the result data. A deviation from a normal topographic distribution or a deviation from a normal coupling between different areas of the brain may be included in the result data for facilitating the prediction associated with the neurological recovery.

In an embodiment, at least one difference of activity of the slow waves between at least two areas of brain is detected by the data processing unit 100. The at least one difference may be based on amplitude, phase or frequency of the slow waves. The at least one difference at a certain moment may be used to present a suggestion for the administration of the anesthetic drug. The anesthetic drug may be administered by a nursing staff, for example.

In an embodiment, the at least one difference at a certain moment may be used to control input of the anesthetic drug substance at a next moment. The prediction of the neurological recovery level may be based on the detected at least one difference of the activity of the slow waves.

In an embodiment, the result data may be an index or a variable derived from the slow wave activity. The result data may be used to predict a good neurological recovery of the person or a poor neurological recovery of the person. The good neurological recovery of the person is possible if the activity of the slow waves is higher than a predetermined threshold. The predetermined threshold may be decided on the basis of experience. In an embodiment, the predetermined threshold may be at a level where the activity increases more than a certain percentage after any rate of administration of the anesthetic drug substance. In an embodiment, the predetermined threshold may be at a level where the activity increases more than 50%, for example, after any rate of administration of the anaesthetic drug substance. The data processing unit 100 may, in a similar manner, form and output the result data which may be used to predict severe disability, coma or death if the activity of the slow waves is lower than a predetermined threshold. However, the result data, per se, doesn't predict the good or poor outcome but requires a professional's decision of the condition of the person 110.

Figure 7:
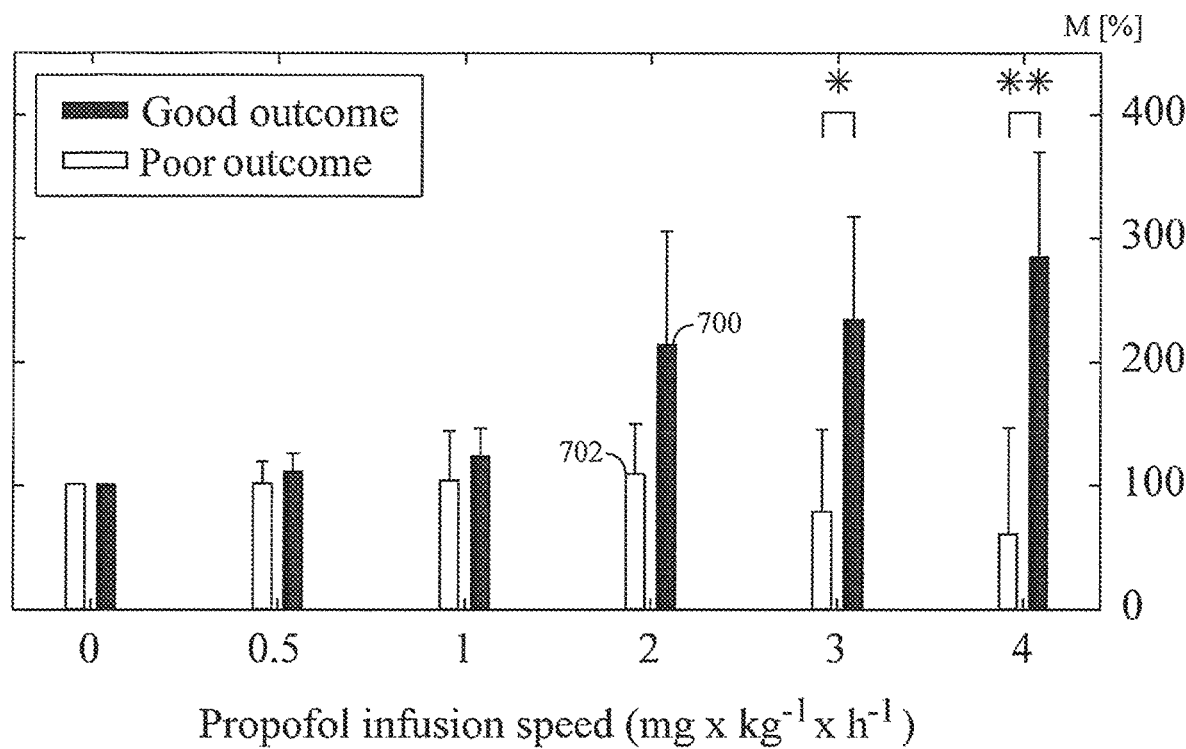
FIG. 7 illustrates an example of a bar chart of average slow wave activity in a brain of good outcome and in a brain of poor outcome as a function of concentration of the anesthetic drug substance.

FIG. 7 is a bar diagram illustrating examples with black bars 700 and white bars 702 which represents changes in activity of the slow waves with respect to different infusion rates denoted in the horizontal axis 0 to 4 mg/kgh. The values represent individual average powers calculated from a plurality of channels given relative to the individual average power at propofol infusion rate 0 mg/kgh. Bars show group means and standard deviations. Asterisks indicate statistically significant difference between groups of good outcome and poor outcome (*P<0.05, **P<0.01).

The person with the result of the black bars 700 can be expected to result in a good outcome because the activity of the slow waves substantially increases with the increasing concentration of the anesthetic drug substance. The person with the white bars 702, in turn, can be expected to result in a poor outcome because the activity of the slow waves doesn't substantially increase with the increasing concentration of the anesthetic drug substance.

In an embodiment, the data processing unit 100 may form and output the result data which may be presented to the nursing staff. The result data may include one or more alphanumeric symbols. The staff may use the result data to predict the neurological recovery of the person 110. An example of the result data is shown in Table 1, wherein the result data has five categories C1 to C5. The categories may be used to predict a range from a return of normal cerebral function and normal living to death.

In an embodiment, the data processing unit 100 may also predict the outcome on the basis of the measurement and/or the result data.

Table 1 below illustrates an example of the result data with five categories C1 to C5 and the expected or predicted neurological recovery level.

TABLE 1

Cerebral Performance Category (CPC)

| | |
|---|---|
| C1 | Return of normal cerebral function and normal living |
| C2 | Disability but sufficient function for independent daily activities |
| C3 | Severe disability |
| C4 | Coma |
| C5 | Death |

The severity of the brain injury may be determined by evaluating the neurological recovery six months after the cardiac arrest using the Cerebral Performance Category above as recommended by the American Heart Association, for example. The patients may be predicted to belong to or assigned to either good (C1-C2) or poor (C3-C5) outcome groups depending on if they are independent in activities of daily living after the control period or not.

In the patients with good neurological outcome, the low-frequency (<1 Hz) EEG power representing the slow wave activity can be found to significantly decrease when the amount of propofol was reduced. While the absolute effect is most pronounced in the prefrontal and temporal areas in which the slow wave activity was strongest at high propofol infusion rates, a clear relative change can be observed in all channels regardless of the brain region. Compared to the individual values at infusion rate 0 mg/kgh, the propofol-induced increase in the average low-frequency power at maximum infusion rate (4 mg/kgh) is 183.1±84.3% in the example of FIG. 7.

Unlike those who recovered well, the patients with poor neurological outcome are unable to generate substantial propofol-induced or, in general, anesthetic-drug-substance-induced slow wave activity. The change in the low-frequency EEG power with respect to the change in concentration of the anesthetic drug substance is non-significant. The average power at maximum infusion rate (4 mg/kgh) is 59.9±86.0% compared to the individual values at infusion rate 0 mg/kgh in the example of FIG. 7. Consequently, propofol-induced change in the low-frequency power can be considered to have a statistically significant difference between those who recovered well and those who had the poor outcome.

In addition to or instead of propofol the anesthetic drug substance may be other anesthetics known to affect slow wave activity. In an embodiment, and more generally, the at least one anesthetic drug substance may be selected from the following groups of other intravenous GABAergic anethetics, inhalational GABAergic anethetics, opioids and alpha2-adrenergic anesthetics.

The group of the other intravenous GABAergic anethetics may include etomidate, thiopental, and/or methohexital, for example.

The group of the inhalational GABAergic anethetics may include isoflurane, desflurane, and/or sevoflurane, for example.

The group of the opioids may include morphine, fentanyl, alfentanil, remifentanil, and/or sufentanil, for example.

The group of the alpha2-adrenergic anesthetics may include dexmedetomidine or the like, for example.

Figure 8:
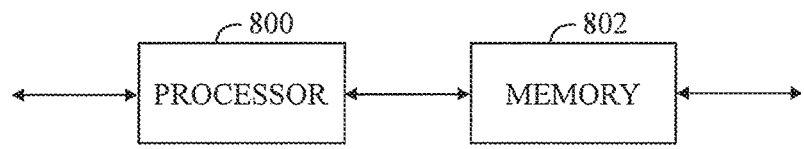
FIG. 8 illustrates an example of a data processing unit.

FIG. 8 illustrates an example of a brain examination apparatus, which may comprise the data processing unit 100. The brain examination apparatus of FIG. 8 comprises at least one processor 800 and at least one memory 802 including a computer program code. The at least one memory 802 and the computer program code cause, with the at least one processor 800 and the at least one memory 802, the brain examination apparatus at least to receive the electroencephalographic data based on a measurement of a person exposed to at least one anesthetic drug substance the concentration of which in the body 110 of the person 108 has at one or more estimated or measured levels as a function of time, and determine and present the activity of the slow waves at the one or more estimated or measured levels of the concentration.

Figure 9:
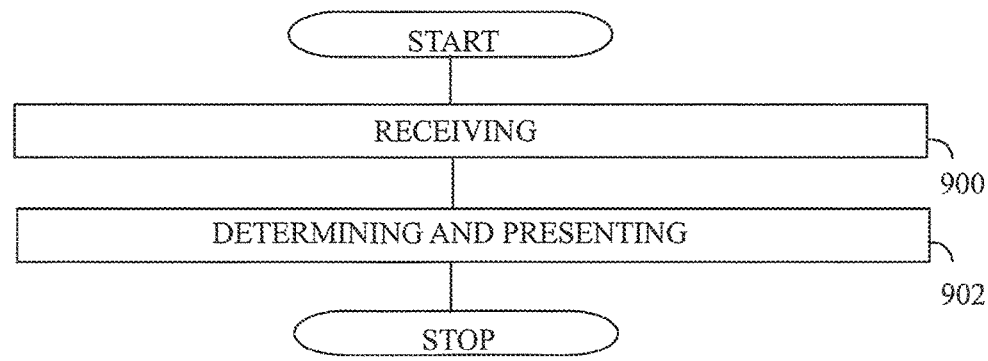
FIG. 9 illustrates an example of a flow chart of the method.

FIG. 9 illustrates an example a flow chart of a method. In step 900, receiving electroencephalographic data based on a measurement of a person exposed to at least one anesthetic drug substance the concentration of which in the body of the person has at one or more estimated or measured levels as a function of time. In step 902, determining and presenting activity of slow waves of the electroencephalographic data at the one or more estimated or measured levels of the concentration.

The method shown in FIG. 9 may be implemented as a logic circuit solution or a computer program.

The computer program may be placed on a computer program distribution means for the distribution thereof. The computer program distribution means is readable by means of a data processing unit, and it may encode the computer program commands to control the operation of the measuring device.

The distribution means, in turn, may be a solution known per se for distributing a computer program, for instance a computer-readable medium, a program storage medium, a computer-readable memory, a computer-readable software distribution package or a computer-readable compressed software package.

Even though the invention has been described above with reference to the examples according to the attached drawings, it is clear that the invention is not restricted thereto but may be modified in many ways within the scope of the accompanying claims.

It will be obvious to a person skilled in the art that, as technology advances, the inventive concept can be implemented in various ways. The invention and its embodiments are not limited to the example embodiments described above but may vary within the scope of the claims.

The invention claimed is:

1. An apparatus comprising:
an administration device configured to cause estimated or measured non-zero amounts of an anesthetic drug substance to be introduced into a body of a person and to adjust input of the anesthetic drug substance into the body; and
at least one processor and associated memory configured to:
receive electroencephalographic data for a brain based on at least one measurement of the person exposed to the estimated or measured non-zero amounts of the anesthetic drug substance, the electroencephalographic data comprising slow waves having a frequency at or below 1 Hz;
control the administration device to introduce continuously into the body the anesthetic drug substance at a rate of from 2 mg/(kg*h) to 4 mg/(kg*h) and to adjust the estimated or measured non-zero amounts of the anesthetic drug substance based on at least one of the following: the electroencephalographic data, activity of the slow waves, and data relating to the estimated or measured non-zero amounts of the anesthetic drug substance;
determine changes in the activity of the slow waves of the electroencephalographic data with respect to the estimated or measured non-zero amounts of the anesthetic drug substance;
predict a good neurological recovery of the person if the activity of the slow waves increases by more than 50% relative to the activity of the slow waves prior to the introduction of the anesthetic drug substance and predict a poor neurological recovery of the person if the activity of the slow waves does not increase by more than 50% relative to the activity of the slow waves prior to the introduction of the anesthetic drug substance; and
present result data that represent the changes and that show (i) whether the activity of the slow waves has increased by more than 50% with the introduction of the anesthetic drug substance, thereby indicating the good neurological recovery, or (ii) whether the activity of the slow waves has not increased by more than 50% with the introduction of the anesthetic drug substance, thereby indicating the poor neurological recovery.

2. The apparatus of claim 1, wherein the at least one processor is further configured to form the result data based on the activity of the slow waves and present the result data for a prediction of a neurological recovery level of the person.

3. The apparatus of claim 1, wherein the at least one processor is further configured to form different pieces of the result data for the increase in the activity of the slow waves being more than 50% and the increase in the activity of the slow waves not being more than 50%.

4. The apparatus of claim 1, wherein the at least one processor is further configured to present the prediction of the good neurological recovery or the poor neurological recovery.

5. The apparatus of claim 1, wherein the at least one processor is further configured to measure the activity of the slow waves based on at least one of the following: amplitude spectrum, frequency spectrum, phase spectrum and a power spectral density of the slow waves.

6. The apparatus of claim 1, wherein the at least one processor is further configured to determine location dependent activity of the slow waves across the surface of the brain and form a topographical map of the location dependent activity of the slow waves to be shown for determining and presenting the result data.

7. The apparatus of claim 1, wherein the at least one processor is further configured to control the administration device to:
introduce continuously into the body the anesthetic drug substance at a rate of from 3 mg/(kg*h) to 4 mg/(kg*h); and
predict the good neurological recovery of the person if the activity of the slow waves has increased at least by a factor of 2 relative to the activity of the slow waves prior to the introduction of the anesthetic drug substance and predict the poor neurological recovery of the person if the activity of the slow waves has not increased at least by a factor of 2 relative to the activity of the slow waves prior to the introduction of the anesthetic drug substance.

8. The apparatus of claim 1, wherein during the introduction of the anesthetic drug substance into the body, the at least one processor is further configured to control the administration device to change the rate of introduction of the anesthetic drug substance.

9. The apparatus of claim 8, wherein the at least one processor changes the rate of introduction by decreasing the rate at which the anesthetic drug substance is introduced into the body.

10. The apparatus of claim 8, wherein the at least one processor changes the rate of introduction by increasing the rate at which the anesthetic drug substance is introduced into the body.

11. A method comprising:
causing estimated or measured non-zero amounts of an anesthetic drug substance to be introduced continuously into a body of a person at a rate of from 2 mg/(kg*h) to 4 mg/(kg*h);
receiving electroencephalographic data for a brain based on at least one measurement of the person exposed to the estimated or measured non-zero amounts of the anesthetic drug substance, the electroencephalographic data comprising slow waves having a frequency at or below 1 Hz;
adjusting the estimated or measured non-zero amounts of the anesthetic drug substance based on at least one of the following: the electroencephalographic data, activity of the slow waves, and data relating to the estimated or measured non-zero amounts of the anesthetic drug substance;

determining changes in the activity of the slow waves of the electroencephalographic data with respect to the estimated or measured non-zero amounts of the anesthetic drug substance;

predicting a good neurological recovery of the person if the activity of the slow waves increases by more than 50% relative to the activity of the slow waves prior to the introduction of the anesthetic drug substance and predicting a poor neurological recovery of the person if the activity of the slow waves does not increase by more than 50% relative to the activity of the slow waves prior to the introduction of the anesthetic drug substance; and presenting result data that represent the changes and that show (i) whether the activity of the slow waves has increased by more than 50% with the introduction of the anesthetic drug substance, thereby indicating the good neurological recovery, or (ii) whether the activity of the slow waves has not increased by more than 50% with the introduction of the anesthetic drug substance, thereby indicating the poor neurological recovery.

12. The method of claim 11, further comprising presenting the result data for a prediction of a neurological recovery level of the person.

13. A non-transitory computer readable medium having a computer program code stored thereon, the computer program code being configured to cause a computer apparatus to:

cause estimated or measured non-zero amounts of an anesthetic drug substance to be introduced continuously into a body of a person at a rate of from 2 mg/(kg*h) to 4 mg/(kg*h);

receive electroencephalographic data for a brain based on at least one measurement of the person exposed to the estimated or measured non-zero amounts of the anesthetic drug substance, the electroencephalographic data comprising slow waves having a frequency at or below 1 Hz;

adjust the estimated or measured non-zero amounts of the anesthetic drug substance based on at least one of the following: the electroencephalographic data, activity of the slow waves, and data relating to the estimated or measured non-zero amounts of the anesthetic drug substance;

determine changes in the activity of the slow waves of the electroencephalographic data with respect to the estimated or measured non-zero amounts of the anesthetic drug substance;

predict a good neurological recovery of the person if the activity of the slow waves increases by more than 50% relative to the activity of the slow waves prior to the introduction of the anesthetic drug substance and predict a poor neurological recovery of the person if the activity of the slow waves does not increase by more than 50% relative to the activity of the slow waves prior to the introduction of the anesthetic drug substance; and present result data that represent the changes and that show (i) whether the activity of the slow waves has increased by more than 50% with the introduction of the anesthetic drug substance, thereby indicating the good neurological recovery, or (ii) whether the activity of the slow waves has not increased by more than 50% with the introduction of the anesthetic drug substance, thereby indicating the poor neurological recovery.

* * * * *